United States Patent [19]

Harisiades et al.

[11] Patent Number: 5,266,715
[45] Date of Patent: Nov. 30, 1993

[54] GLASS COATING WITH IMPROVED ADHESION AND WEATHER RESISTANCE

[75] Inventors: Paul Harisiades, Seattle, Wash.; Kirtland P. Clark, Bethel, Conn.

[73] Assignee: Ciba-Geigy Corporation, Ardsley, N.Y.

[21] Appl. No.: 665,493

[22] Filed: Mar. 6, 1991

[51] Int. Cl.$^5$ ............ C07F 7/08; C07F 7/10; C07F 7/18
[52] U.S. Cl. .................. 556/419; 556/420; 556/421; 556/414; 556/427
[58] Field of Search ............ 556/421, 420, 427, 419, 556/414

[56] References Cited

U.S. PATENT DOCUMENTS

| | | | |
|---|---|---|---|
| 2,966,507 | 12/1960 | Montgomery | 556/421 |
| 3,046,250 | 7/1962 | Plueddemann | 556/421 X |
| 3,208,971 | 9/1965 | Gilkey et al. | 220/465 |
| 3,576,033 | 4/1971 | Tesoro et al. | 260/448.8 |
| 4,213,914 | 7/1980 | Bargain et al. | 556/421 X |
| 4,316,041 | 2/1982 | Totten et al. | 556/421 X |
| 4,496,611 | 1/1985 | Kawakubo et al. | 427/160 |
| 4,506,058 | 3/1985 | Ashby et al. | 524/730 |
| 4,623,740 | 11/1986 | Deschler et al. | 556/421 |
| 4,650,889 | 3/1987 | Plueddemann | 556/421 |
| 4,735,979 | 4/1988 | Beers et al. | 556/421 X |
| 4,847,396 | 7/1989 | Beers et al. | 556/421 |
| 5,019,637 | 5/1991 | Panster et al. | 556/421 X |
| 5,070,169 | 12/1991 | Robertson et al. | 556/421 X |
| 5,070,170 | 12/1991 | Robertson et al. | 556/421 X |
| 5,166,383 | 11/1992 | Parrinello et al. | 556/421 X |

*Primary Examiner*—Paul F. Shaver
*Attorney, Agent, or Firm*—Luther A. R. Hall

[57] ABSTRACT

A novel coating for glass with an adhesive strength of >45 Kg/cm$^2$ and improved resistance to moisture and sunlight, which may contain opacifying pigments for decorating glass surfaces, is a hard (Shore D 84), cross-linked siloxane-urea, siloxane-urethane, siloxane-sulfide or siloxane-amide which adheres covalently to the glass surface and is resistant to scratching and delamination.

10 Claims, 2 Drawing Sheets

GLASS COATING WITH IMPROVED ADHESION AND WEATHER RESISTANCE

BACKGROUND OF THE INVENTION

The instant invention relates to a coating composition for glass, and more particularly, to such coatings utilizable on glass surfaces for decorative purposes.

Decorative surfaces on preformed glass articles are widely used in the beverage industry. Presently such surfaces are made by sintering glass particles and pigments onto the surface, a process which requires much energy and also releases toxic compounds. A less energy intensive and safer process would be highly desirable, as long as the product can withstand the requirement of repeated cleaning cycle without deterioration. It is an objective of the present invention to provide a polymeric coating on glass which can fulfill their requirements.

Another objective of this invention are glass coatings or sealants which will last much longer than those presently in use, such as poly(sulfides), poly(urethanes), or poly(ethylene) which do not maintain adhesion to glass for any practical length of time. Even the more advanced silicone-type coatings, which contain glass-reactive alkoxysilane groups are not entirely satisfactory in performance; effects of weather cause, with time, adhesive failure. Futhermore, problems such as blotchiness, mottling, poor scratch resistance, and other unsightly conditions detract from the utility of these coatings in practice.

Thus, there is a marked deficiency in the products of the prior art and there is a definite need for a coating that will adhere to glass for a long period of time, and will have a high resistance to moisture, sunlight, and abrasion.

SUMMARY OF THE INVENTION

Accordingly, an object of this invention is to eliminate the aforementioned and other disadvantages and deficiencies of the prior art products. This has been achieved by creating a coating that bonds covalently to the surface of the glass. Furthermore, the bond linking the coating to the substrate is a siloxane (Si-O-Si) bond which is of high strength and highly resistant to hydrolysis. This chemistry is analogous to that of silane coupling agents used to imbed glass fiber in polymer matrices, with the exception that much greater adhesion is possible with the coatings of the instant invention.

Silane primers for glass have been described by Kawakubo et. al. in U.S. Pat. No. 4,496,611. However the adhesive strength in this system was maximally 7.3 Kg/cm$^2$ and, more importantly, no claims or tests were made about the hydrolytic resistance of this primer. In the instant invention, coatings with adhesive strengths of >45 Kg/cm$^2$ even after exposing the coated plates to 100% humidity at 200° F. (93° C.) for one week have been achieved. Furthermore these coatings possess very high resistance to photolytic delamination when used in conjunction with commercial UV absorbers and light stabilizers. Slight diminution in adhesive strength is observed only after a 5000 hour exposure to a Xenon arc light in a Weather-o-meter; this corresponds to approximately three years of exposure to Florida sunlight. In the prior art (U.S. Pat. No. 4,496,611) exposures of 540 hours of sunshine are reported with no adhesive loss to the primer.

A further advantage of the instant invention over the prior art is the hardness of the coating and its resistance to abrasion. Considerable deficiencies and difficulties presently exist with the aforementioned pressure sensitive opacified films in terms of blotchiness, mottling, and delamination. These deficiencies are obviated by the coating of the instant invention which has a Shore D hardness of 84 and a glass transition temperature of 104° C.

By using a coating composition of this invention in conjunction with commercial UV light absorbers and stabilizers, it is possible to satisfy the three most important factors necessary for a glass sealant: namely, a high resistance to moisture, a high resistance to sunlight, and a high resistance to abrasion. Furthermore, the coating can be used unpigmented where water white transparency is desired, or may be pigmented where an opacified coating is desired. The latter is usually the case where decorative architectural spandrel is concerned, and it has been found that the incorporation of an inorganic pigment up to 25% by weight does not diminish the adhesion or weatherability of the final coating. Complete opacification is achieved with only 20% pigment, for example titanium dioxide, providing the pigment is dispersed in the solubilized coating composition prior to application.

The film forming component is described as an organo-siloxane copolymer, preferably a siloxane urea, but in contrast to the siloxane coatings mentioned earlier, the instant coating is hard (Shore D 84), and adheres covalently to the glass surface through siloxane bonds. While siloxane bonding adhesion is possible with conventional coupling agents, the instant invention is superior to these in that the instant film forming substance offers a greater degree of molecular organization which provides not only stronger adhesion, but also a greater resistance to hydrolysis and delamination.

DETAILED DESCRIPTION OF THE INVENTION

The instant invention pertains to a composition for coating glass which is the reaction product of two components. The first component is a trialkoxysilyl adduct which may be linear or branched; the second component is a polysiloxanediol or silanediol. The first component is a compound of formula A $$[(EO)_3\text{-Si-R-X-}]_k T \qquad (A)$$

wherein k is 2 to 4,

E is methyl or ethyl,

R is ethylene or trimethylene,

X is —NHCONH—, —NHCOO—, —S—, —NHCO— or a direct bond, where the —NH— group is attached to R, and T is, when k is 2 and X is a direct bond, —NHCONH—, or T is, when X is —NHCONH—, the residue of a diisocyanate or a triisocyanate after removal of 2 or 3 NCO groups, or T is, when X is —NHCOO—, the residue of a diol, triol or tetraol or of a isocyanate or a poly(dimethylsiloxane) alkanepolyol after removal of 2, 3 or 4 OH groups, or T is, when X is —S—, alkylene of 1 to 12 carbon atoms, alkanetriyl of 3 to 8 carbon atoms or alkanetetrayl of 4 to 10 carbon atoms, or T is, when X is —NHCO—, alkylene of 2 to 10 carbon atoms or arylene of 6 to 10 carbon atoms.

The second component needed to prepare the instant coating composition is a compound of the formula B $$\text{HO-[Si(L)}_2\text{-O-]}_n\text{-H} \quad \text{(B)}$$

wherein
n is 1 to 100, and
L is methyl, isopropyl, —CH$_2$CH$_2$CF$_3$, tert-butyl, cyclohexyl or phenyl.

Preferably n is 1 and L is phenyl.

The reaction of the first and second components forms a compound of formula $$[\text{HO[Si(L)}_2\text{-O-]}_n\text{-Si(OE)}_2\text{R-X-}]_k\text{T} \quad \text{(I)}$$

where L, R, X, T, n and k are as defined above.
Preferably, k is 2 or 3, most preferably 2.
Preferably E is ethyl.
Preferably R is trimethylene.
Preferably X is —NHCONH— or —NHCOO—, most preferably —NHCONH—.
Preferably when X is —NHCONH—, T is a residue of a diisocyanate.
Preferably when X is —NHCOO—, T is the residue of a diol.
Preferably when X is —S—, T is alkylene of 1 to 8 carbon atoms, most preferably alkylene of 2 to 4 carbon atoms.
Preferably X is —NHCO—, T is alkylene of 2 to 8 carbon atoms, most preferably alkylene of 4 to 6 carbon atoms.

The siloxane bond formation which occurs during cure is essential for the grafting of silanol groups on the glass surface. A 10/1 to 3/1 excess of alkoxysilyl groups in the compound of formula (A) to silanol groups in the compound of formula B are used to ensure maximum grafting to the glass surface by siloxane bond formation.

Suitable disilanols of formula B include oligomeric polysiloxane diols, silane diols such as di-isopropyl, di-t-butyl, dicyclohexyl, and diphenyl silanols di (or silane diol), and 1,4-bis(hydroxydimethylsilyl) benzene. Preferred diols include diphenyl silane diol and 1,4-bis(-hydroxydimethyl-silyl) benzene; the most preferred being diphenyl silane diol.

The trialkoxysilyl macromers of formula A are prepared by reacting coupling agents of various functionality with suitable organic substrates. In this manner linear and branched macromers capped with trialkoxysilyl groups are formed.

Examples of condensation reaction linkages used to form the adduct of formula I include amide, ester, amine, urethane, urea, sulfide, sulfone, sulfamide, phosphoramide, siloxane, and alkyl (from hydrosilation), which may be found singly or in combination with each other.

Preferred are urea and urethane groups, most preferred are urea groups.

Preferably, the instant invention pertains to glass, having a hard, strongly adhering, scratch- and delamination-resistant coating, which coating comprises the cure siloxane-urea polymerization product of a compound of formula I $$\left[ \text{T} \stackrel{|}{-} \text{NHCONH(CH}_2)_3 \stackrel{|}{-} \underset{\underset{\text{OC}_2\text{H}_5}{|}}{\overset{\overset{\text{OC}_2\text{H}_5}{|}}{\text{Si}}} \stackrel{|}{-} \text{O} \stackrel{|}{-} \underset{\underset{\text{C}_6\text{H}_5}{|}}{\overset{\overset{\text{C}_6\text{H}_5}{|}}{\text{Si}}} \stackrel{|}{-} \text{OH} \right]_k \quad \text{(I)}$$

wherein T is the k-valent radical of a di- or tri-isocyanate T(NCO)$_k$ after removal of the two or three NCO groups, and k is 2 or 3, said cured coating being crosslinked and covalently bonded to the glass through siloxane bonds.

BRIEF DESCRIPTION OF DRAWING

The instant coating is attached to the surface of the glass as seen schematically in FIG. 1.

The crosslinked coating is seen in FIG. 2.

REACTION COMPONENT A

Figure 1:
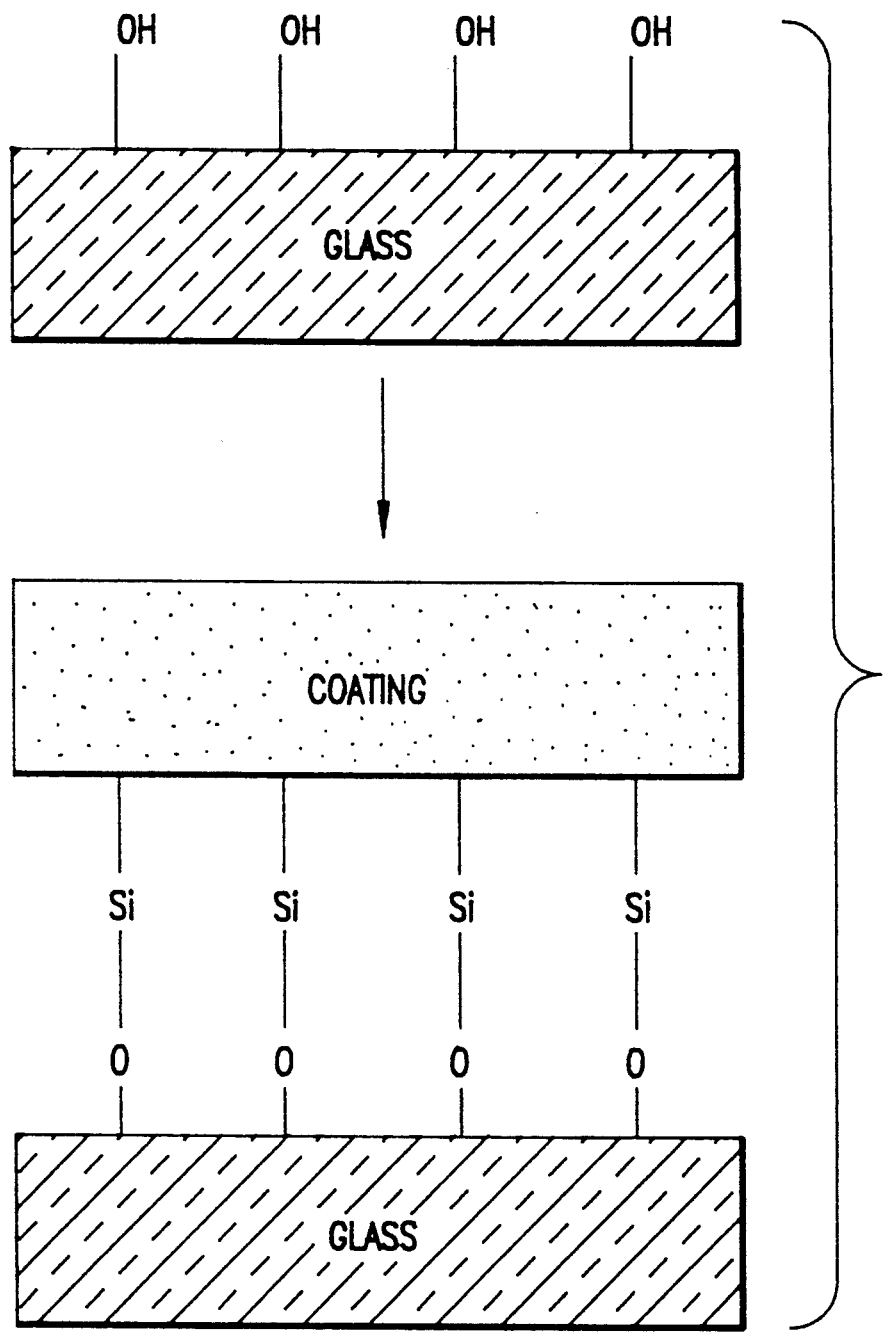

The film forming substance of this invention, described as a siloxane-urea copolymer (X=—NHCONH—) is formed in two distinct steps prior to curing. In the first step, a triethoxysilyl-urea (TEOS) adduct of formula A is prepared from a di- or tri-isocyanate and 3-aminopropyltriethoxysilane:

$$2(\text{EtO})_3\text{Si}-(\text{CH}_2)_3\text{NH}_2 + \text{T(NCO)}_k \longrightarrow$$

$$\text{T}\left[ \text{NH} \stackrel{|}{-} \underset{\underset{\text{O}}{\|}}{\text{C}} \stackrel{|}{-} \text{NH}-(\text{CH}_2)_3\text{Si(OEt)}_3 \right]_k$$

where k is 2 or 3.

Diisocyanates or triisocyantes useful to form the compounds of formula I are aliphatic, cycloaliphatic or aromatic polyisocyanates. T is a radical derived from T(NCO)$_k$ after removal of two or three NCO groups and is derived from a diisocyanate, triisocyanate or mixture thereof selected from the group consisting of ethylene diisocyanate, 1,2-diisocyanato-propane, 1,3-diisocyanatopropane, 1,6-diisocyanatohexane, 1,2-diisocyanato-cyclohexane, 1,3-diisocyanato-cyclohexane, 1,4-diisocyanatobenzene; bis (4-isocyanatocyclohexyl)methane, bis-(4isocyanatocyclohexenyl) methane, bis(4-isocyanatophenyl)-methane, 1,2- and 1,4-toluene diisocyanate; 3,3'-dichloro-4,4'-diisocyanatobiphenyl; tris(4-isocyanatophenyl)methane, 1,5-diisocyanato-naphthalene, hydrogenated toluene diisocyanate; 1-isocyanatomethyl-5-isocyanato-1,3-3-trimethylcyclohexane (=isophorone diisocyanate); 1,3,5-tris(6-isocyanatohexyl) biuret, 1,6-diisocyanato-2,2-4-(2,4,4)-trimethyl-hexane, 2,2'-diisocyanatodiethyl fumarate; 1,5-diisocyanato-1-carboxypentane; 1,2-, 1,3-, 1,6-, 1,7-, 1,8-, 2,7- and 2,3 diisocyanatonaphthalene; 2,4- and 2,7-diisocyanato-1-methylnaphthalene; 1,4-diisocyanatomethylcyclo-hexane; 1,3diisocyanato-6(7)-methylnaphthalene; 4,4'diisocyanatobiphenyl; 4,4'-diisocyanato-3,3'-dimethoxy-bisphenyl; 3,3'- and 4,4'-diisocyanato 2,2'-dimethyl biphenyl; bis-(4-isocyanatophenyl) ethane; and bis(4-isocyanatophenyl) ether.

Preferably T is the radical derived from dicyclohexylmethane-4,4'-diisocyanate.

In like manner, adducts A wherein X is —NHCOO— are made from polyois; adducts A wherein X is —S— from polyhalogen compounds, and adducts A wherein X is —NHCO— from diesters.

Typical polyols are: 1,2 Butanediol, 1,3-butanediol, 1,4 butanediol, 1,2-cyclohexane diol, 1,2-cyclooctanediol, 1,3-cyclopentanediol, 1,2-decanediol, 1,10-decanediol, dicyclohexyl-4,4'-diol, 2,2-diethyl-1,3-propane diol, 2,5-dimethyl-2,5-hexanediol, 2,4-dimethyl-2,4-pentane diol, ethylene glycol, 1,7-heptanediol, 1,2-hexanediol, 1,5-hexanediol, 1,6-hexanediol, 2-methyl-2,4-pentanediol, 1,8-octanediol, pentaerythritol, 1,5-pentanediol, 1,14-tetradecanediol, polyethylene glycol, polypropylene glycol, polybutylene glycol, nepentyl glycol, trimethyololropane, or poly(dimethylsiloxane) alkanepolyols of structures adducts A wherein X is —NHCOO— are made from polyols;

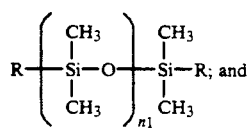

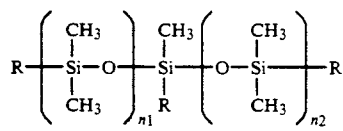

wherein
R=—CH$_2$CH$_2$CH$_2$OH, —CH$_2$CH$_2$CH(OH)CH$_3$, (CH$_2$)$_3$O—CH$_2$—CH(OH)CH$_2$OH, (CH$_2$)$_3$N(CH$_2$CH$_2$OH)$_2$) or (CH$_2$)$_4$—CH(OH)CH$_2$OH, and $n_1$ and $n_2$ are integers from 2 to 50,
with the proviso that $n_1 + n_2$ is not greater than 60.

Typical polyhalogen compounds are: 1,4-dibromobutane, 1,2-dibromoethane, 1,3-dibromopropane, 1,10-dibromodecane, 1,12-dibromododecane, 1,6-dibromohexane, 1,5-dibromopentane, 1,3-dibromopropane, 1,11-dibromoundecane, 1,4-dichlorobutane, 1,10-dichlorodecane, 1,2-dichloroethane, 1,6-dichlorohexane, 1,3-dichlorohexane, 1,4-diiodobutane, 1,10-diiododecane, 1,6-diiodohexane, diiodomethane, 1,8-diiodooctane, 1,5-diiodopentane, 1,3-diiodopropane, poly(vinyl chloride).

Typical diesters are: diethyl adipate, diethyl azelate, diethyl carbonate, diethyl malonate, diethyldodecanedioate, diethyl fumarate, diethyl glutarate, diethyl oxalate, diethyl sebacate, diethyl suberate, diethyl succinate, diethyl tartrate, dimethyl adipate, dimethyl azelate, dimethyl carbonate, dimethyl malonate, dimethyldocecane dioate, dimethyl fumarate, dimethyl glutarate, dimethyl oxalate, dimethyl sebacate, dimethyl suberate, dimethyl succinate, dimethyl tartrate.

The starting materials for preparing the instant adducts of formula A and the compounds of formula I are largely items of commerce.

The adduct product is either a clear, viscous liquid or a hard, white solid depending on the rigidity of the diisocyanate employed. These triethoxysilane (TEOS) urea adducts are stable indefinitely when stored in glass or plastic containers at room temperature. They are readily soluble in organic solvents with dielectric constants greater than or equal to that of chloroform. Most preferred is ethanol due to its volatility and low toxicity.

SYNTHESIS OF COATING COMPOUND I

The second step of the coating synthesis involves the reaction of the TEOS adduct A with diphenylsilanediol (or another compound 3) to give a typical compound of formula I, for example:

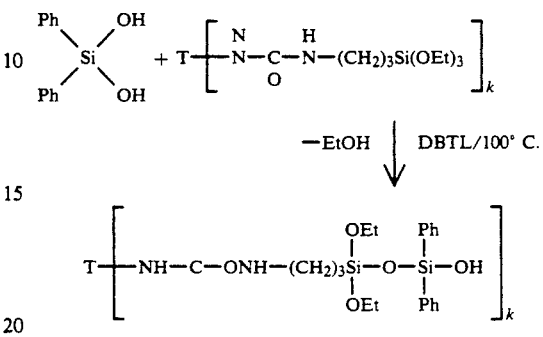

where T and k are defined as described above.

At this preliminary stage of reaction the viscosity of the coating composition decreases dramatically, and a clear, viscous liquid product is obtained. At this point, the viscosity can be adjusted by the addition of solvent to provide the proper conditions for the dispersion of a pigment, if an opaque coating is desired.

By including various pigments and dyes in the composition of this invention, as desired, it is possible to adjust color hues and increase the weather-resistant adhesion of a cured overcoating. Examples of pigments which may be used in the glass coating composition include inorganic pigments, such as chromic acid salts, ferrocyanides, sulfides, sulfuric acid salts, oxides (e.g. titanium white, red iron oxide), double oxides (e.g. titanium yellow), hydroxides, carbonates, silicic acids, carbon (e.g. carbon black), and metal powders; and organic pigments, such as nitroso compounds, nitro compounds, azo compounds, condensed azo compounds, quinacridone compounds, isoindolinone compounds, anthraquinone compounds, and phthalocyanine compounds. These pigments may be used singly or in combination. It is possible to shield a desired part of the light bandwidth (i.e. wavelengths greater than 380 nm) by suitable selection of pigments. However, it is essential to use an effective stabilizing amount (usually 0.1 to 5% by weight) of ultraviolet light absorbers and light stabilizers in order to screen out light having wavelengths of 380 nm or less, and thus produce the desired effect of lengthening the time that the coating will maintain its adherence to the glass surface.

Examples of the ultraviolet light absorbing substances utilizable in the instant coating compositions include, for example, 2-(2'-Hydroxyphenyl)-benzotriazoles, like the 5'-methyl-, 3',5'-di-tert-butyl-, 5'-tert-butyl-, 5'-(1,1,3,3-tetramethylbutyl)-, 5-chloro-3',5'-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonylethyl)-, 3'-dodecyl-5'-methyl-, and 3'-tert-butyl-5'-(2-octyloxycarbonyl)ethyl-, and dodecylated-5'-methyl derivatives. Hydroxy-benzophenones, like the 4-hydroxy-, 4-methoxy-4-octoxy, 4-decyloxy-4-dodecyloxy-, 4-benzyloxy, 4,2',4'-trihydroxy- and 2'-hydroxy-4,4'-dimethoxy derivatives. Esters of optionally substituted benzoic acids like phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

Acrylates, like α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline. Nickel compounds, like nickel complexes of 2,2'-thio-bis-(1,1,3,3-tetramethylbutyl)-phenol), such as the 1:1 or 1:2 complex, optionally with additional ligands such as n-butylamine, triethanolamine or N-cyclohexyl-diethanolamine, nickel dibutyldithio-carbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

Sterically hindered amines, like bis-(2,26,6 tetramethyl-piperidyl) sebacate, bis-(1,2,2,6,6-pentamethylpiperidyl) sebacate, n-butyl-3,5-di-tert. butyl-4-hydroxybenzyl malonic acid bis-(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethyl-piperidyl)-hexamethylylenediamine and 4-tert-octylamino-2,6-dichloro-s-triazine, tris-(2,2,6,6-tetramethyl-piperidyl)-nitrilotriacetate, tetrakis-(2,2,6,6-tetramethyl-4-piperidyl)-1,2,3,4-butane-tetracarbonic acid, 1,1'-(1,2-ethanediyl)-bis-(3,3,5,5-tetramethyl-piperazinone).

Oxalic acid diamides, like 4,4'-di-octyloxy-oxanilide, 2,2'-di-octyloxy-5,5'-di-tert-butyl-oxanilide, 2,2'-didodecyloxy-5,5'-di-tert-butyl-oxanilide, 2-ethoxy-2'-ethyloxanilide, N,N'-bis-(3-dimethylamino-propyl)-oxalamide, 2-ethoxy-5-tert-butyl-2'-ethyloxanilide and its mixture with 2-ethoxy-2'-2'-ethyl-5,4'-di-tert-butyloxanilide and mixtures of ortho- and paramethoxy- as well as of o- and p-ethoxy-disubstituted oxanilides.

Hydroxyphenyl-s-triazines, like 2,6-bis-(2,4-dimethyl-phenyl)-4-(2-hydroxy-4-octyloxyphenyl)-s-triazine; 2,6-bis-(2,4-dimethyl-phenyl)-4-(2,4-dihydroxyphenyl)-s-triazine; 2,4-bis(2,4-dihydroxyphenyl-6-(4-chloro-phenyl)-s-triazine; 2,4-[bis(2-hydroxy-4-(2-hydroxyethoxy)phenyl)]-6-(4-chlorophenyl)-s-triazine; 2,4-bis[2-hydroxy-4-(2-hydroxyethoxy)-phenyl]-6(4-bromo-phenyl)-s-triazine; 2,4-bis[2-hydroxy-4-(2-hydroxyethoxy)-phenyl]-6(4-bromophenyl)-s-triazine; 2,4-bis[2-hydroxy-4-(2-acetoxy-ethoxy)-phenyl]-6-(4-chloro-phenyl)-s-triazine, 2,4-bis(2,4-dihydroxyphenyl)-6-(2,4-dimethyl-phenyl)-s-triazine.

These ultraviolet absorbers and light stabilizer compounds may be used singly or preferably in combination with each other.

SYNTHESIS OF COATING

Figure 2:
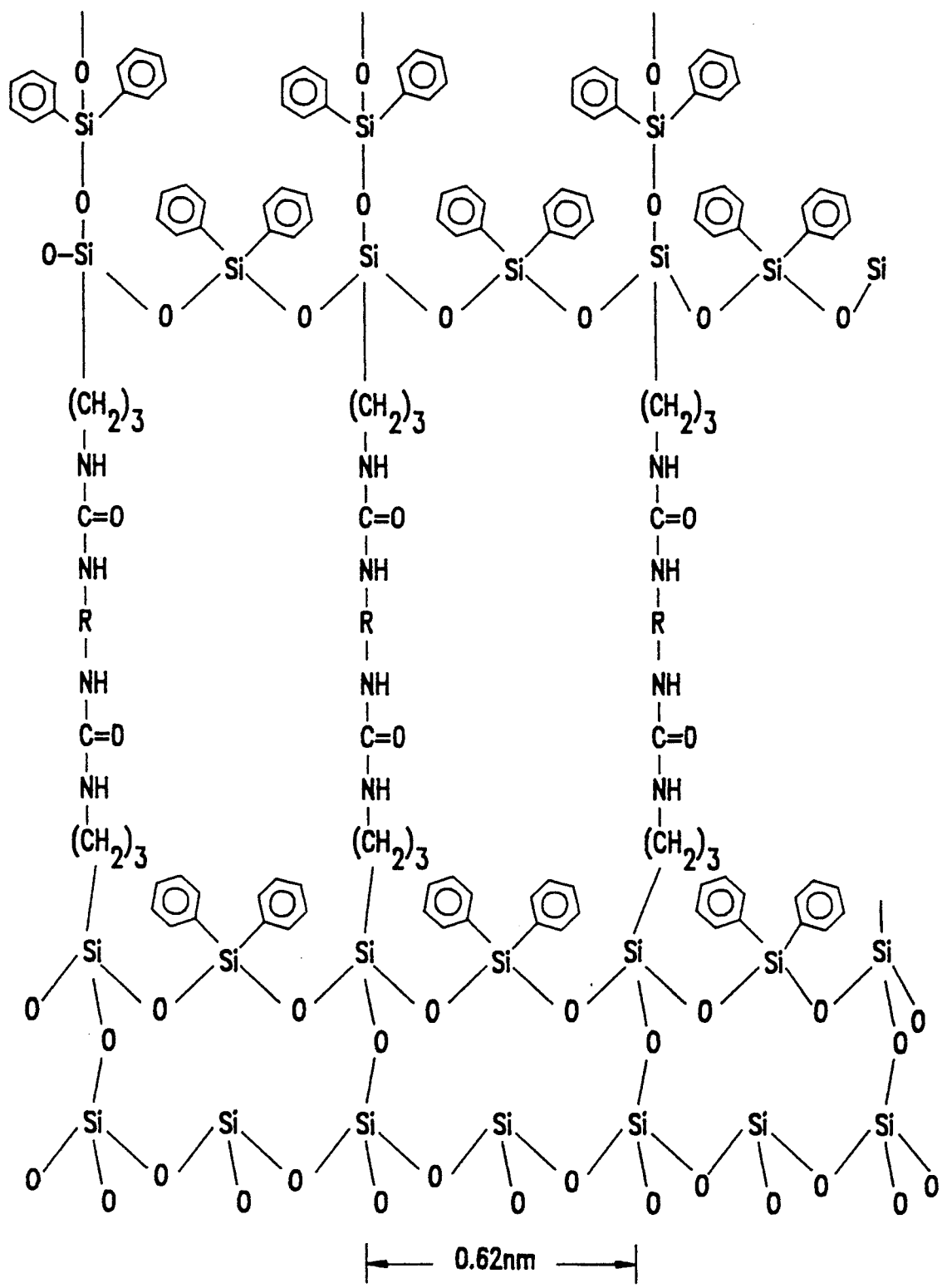

The curable siloxane composition is readily applied to the glass substrate by spreading with a drawing knife of appropriate thickness and then curing in a nitrogen atmosphere at 130° C. The siloxane bond formation that occurs during the cure insures a high degree of grafting to the surface silanol groups on the glass surface by the ethoxy-silyl groups in the coating composition. Furthermore, at this cure temperature, an alternating diphenyl siloxane-urea siloxane crosslinked network is formed, providing a high degree of molecular organization. This arises from the fact that diphenyl silane diol is sterically hindered from self-condensation and that triethoxysilyl groups do not self condense at 130° C. Therefore a tightly crosslinked, alternating, diphenyl siloxane-urea polymer is formed (see FIG. 2) that is highly resistant to hydrolysis. In contrast to conventional coupling agents, where the alkoxy silyl group is hydrolyzed prior to application, a higher degree of molecular organization is achieved through the ethoxysilyl-silanol reaction of this invention. The fact that grafting onto the glass substrate and crosslinking of the coating occur by the same mechanism (i.e. siloxane bond formation) allows the stoichiometry of the curing composition to be tailored to permit a maximal degree of grafting and crosslinking. By using 0.67 equivalents of diphenyl-silanediol to 1.00 equivalent of TEOS adduct, an optimal hardness and adhesion is achieved.

Adhesion is also enhanced by activating the surface of the glass spandrel by generating the maximal number of silanol groups. This is readily achieved by soaking the spandrel in 30% ethanolic potassium hydroxide solution followed by rinsing with water, then soaking in 2.0N sulfuric acid and finally rinsing with distilled water. The clear, activated glass surface has an advancing contact angle of 10° with water.

Siloxane bond formation in the curing step is essential to the development of a stable, covalently bonded, graft to the glass substrate. The fact that the siloxane graft bond forms more slowly and more regularly than is possible with coupling agents insures greater adhesion and reproducibility than is possible with the latter.

The instant invention also pertains to glass compositions coated with a curable compound of formula I which compound upon curing and crosslinking adheres through covalent siloxane bonds to the glass surface.

EXAMPLE 1

Activation of Glass Substrate

Into a 30% solution of ethanolic potassium hydroxide solution are placed pieces of glass spandrel which had previously been washed with soap and water. After soaking for 24 hours in the said solution, the spandrel is removed and rinsed with tap water. The water runs off the glass without retracting. Next the spandrel is soaked in 2N sulfuric acid solution for one hour and the rinsed thoroughly with deionized water. Finally the spandrel is rinsed with acetone and allowed to air dry. Its surface now contains a maximal concentration of silanol groups to permit the highest possible degree of grafting to the coating.

EXAMPLE 2

Preparation of TEOS-Bis (Urea) Adduct

Into a 1000 mL, three necked, round bottomed flask equipped with mechanical stirrer, reflux condenser, dropping funnel with pressure equalizer, is charged dicyclohexylmethane-4,4'-diisocyanate (54.48 g, 0.226 mole) in 185 g of dry, 1,1,1-trichloroethane (TCE). The solution is vigorously stirred, and then aminopropyltriethoxysilane (100.40 g, 0.454 mole) is added dropwise over a period of 60 minutes. A clear, colorless bis (urea) adduct is obtained at 45.59% solids with the following structure:

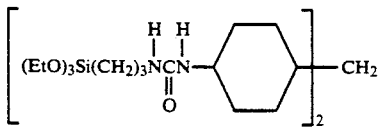

EXAMPLE 3

Preparation of Adduct with Diphenylsilanediol

The TEOS macromer solution of Example 2 (175.35 g, 0.113 mole of adduct) is mixed with diphenylsilanediol (49.10 g, 0.226 mole, 30% weight %) and 1.29 g (1.00%) of dibutyltin dilaurate (DBTL). The reaction mixture is stirred vigorously in a sealed bottle on a hot plate at 100° C. until a clear, colorless solution is obtained. At 59.43% solids, the coating mixture has a Brookfield viscosity of 1200 cP. This composition has a shelf life of one month when stored in glass containers at room temperature.

EXAMPLE 4

Incorporation and Dispersion of Opacifying Pigment

Into a 5.5" (14 cm) diameter ceramic vessel are placed 118.7 g of MEDIA (½" (1.27 cm) diameter ceramic spheres) and 94.61 g of the HMDI-TEOS-diphenylsilane-diol adduct composition of Example 3 (59.43% solids). Then titanium dioxide, TiO2 pigment, Drakenfeld R-960 (14.05 g, 20% with respect to solids) is added and the mixture ball milled at 107 RPM overnight. The pigment-dispersed, opacified coating composition is filtered from the media through a wire mesh screen with a recovery of 88.4%. The percent solids by weight including the 20% TiO2 pigment is 64.74%. Finally, bis (1-octyloxy-2,2,6,6-tetramethylpiperidin-4-yl) sebacate, a hindered amine light stabilizer and 2-[2-hydroxy-3-tert-butyl-5-(2-(omega-hydroxy-octa(ethyleneoxy)carbonyl)-ethylphenyl]-2H-benzotriazole, a benzotriazole UV absorber are incorporated at 2% and 3%, by weight, respectively, with respect to total resin solids. This light stabilized and opacified coating composition is stable at room temperature with a Brookfield viscosity of 1300 cP for 30 days.

EXAMPLE 5

Curing of Coating Composition

A. The opacified coating composition of Example 4 is drawn to a 3 mil (0.076 mm) thickness with a drawing knife over the surface of the activated glass spandrel described in Example 1. The coated spandrel is placed in a 130° C. oven with a nitrogen atmosphere for six hours. A hard, glossy, white finish is obtained. After cooling to room temperature, the adhesive strength is measured at >640 psi with an Elcometer, and the hardness measured at Shore D. 84, Tg 104° C., d=1.51, n=1.56.

B. The cure time is reduced to 1.5 hours by incorporating 1% by weight of stannous octoate immediately before drawing. This catalyst significantly increases viscosity at room temperature after 8 hours and gels within 24 hours. No diminishment of properties is observed compared to the coating formed in part A.

| Composition | Coating for Spandrel |
|---|---|
| | $$\left[ CH_2 \begin{array}{c} \\ \\ \end{array} C_6H_{10}-NH-\overset{O}{\underset{\|}{C}}-NH(CH_2)_3-\underset{\underset{OEt}{\|}}{\overset{\overset{OEt}{\|}}{Si}}-O-\underset{\underset{Ph}{\|}}{\overset{\overset{Ph}{\|}}{Si}}-OH \right]_2$$ |
| Tg | 104° C. |
| Viscosity | 1300 cP |
| | 64% solids in Cl3CCH3 + 20% pigment |
| Hardness | Shore D 84 |
| | (20% TiO2) |
| Adhesive Strength (PSI) | >45 |
| | >45 (100% humidity/93° C., one week) |
| | 15 (5000 hours Weather-o-Meter) |
| | >20 (5000 hours Weather-o-Meter, unpigmented) |
| | 50 (2 days boiling water) |
| Cure | 130° C./1.5 hours |
| Catalyst | 1% Dibutyltin dilaurate |
| | 1% Stannous octoate |

EXAMPLE 6

Preparation of Urea-TEOS Macromer

3-Isocyanatopropyltriethoxysilane (12.4 g, 50 mmol) is added dropwise over a period of 25 minutes to vigorously stirred 3-aminopropyltriethoxy-silane (11.6 g, 50 mmol). After sixty minutes, the exothermic reaction is complete yielding a white waxy solid with the following structure:

EXAMPLE 7

Preparation of Urea-Siloxane Coating for Glass

The urea TEOS macromer of Example 6 (5.3 g, 11.3 mmol) is heated to 100° C. and vigorously stirred with diphenylsilanediol (4.9 g, 22.5 mmol). Stannous octoate (0.10 g, 1%) is then added. After 15 minutes a clear, slightly yellow, viscous liquid is obtained with the following structure:

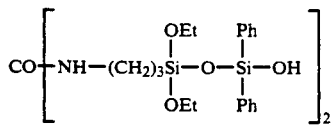

This coating composition is drawn to a 3 mil (0.076 mm) thickness on a clean glass plate and cured for 1.5 hours at 130° C. A clear very hard coating is obtained which is resistant to hydrolytic delamination after exposure to boiling water for 36 hours.

EXAMPLE 8

Preparation of Urethane TEOS Macromer 1,3-Propanediol (2.9 g, 38.0 mmol) is reacted with 3-isocyanatopropyltriethoxy silane (16.4 g, 76.0 mmol) and 0.2% dibutyltin dilaurate catalyst. The reaction is conducted under nitrogen at room temperature in a glass vessel with mechanical stirring. An exotherm occurs after 15 minutes and the reaction is complete after 2 hours as evidenced by infrared spectroscopy.

The following TEOS macromer is obtained $$[CH_2\text{―}CH_2\text{―}O\text{―}CO\text{―}NH(CH_2)_3Si(OEt)_3]_2$$

as a low viscosity liquid, MW 508.72, which is stable at room temperature.

EXAMPLE 9

Preparation of Polyurethane-polysiloxane Coating for Glass

The urethane TEOS macromer of Example 8 (4.0 g, 7.9 mmol) is vigorously stirred with 0.67 equivalents of diphenylsilanediol (3.44 g, 15.88 mmols) at 100° C. under nitrogen. To the slurry is added dibutyltin dilaurate (75 mg, 1.0%). After 30 minutes ethanol evolves to give a clear liquid coating composition with the following structure:

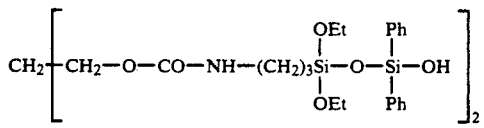

After cooling to room temperature, stannous octoate (75 mg, 1.0%) is dissolved into the composition which is subsequently drawn over a clean glass plate at a thickness of 3 mils (0.076 mn). Curing is preformed at 130° C. for 1.5 hours to give a clear, hard coating which adheres to the glass with a strength of >20 kg/cm². The coating is resistant to hydrolysis upon exposure to boiling water for 24 hours.

EXAMPLE 10

Preparation of Poly(dimethylsiloxane) EOS Macromer

Into a glass reactor is placed poly(dimethylsiloxane) dipropanol (54.7 g, 66.7 mmol) Shin-Etsu X-22-160AP MW 820 and 3-isocyanatopropyl triethoxy silane (33.0 g, 133.4 mmol) with dibutyltin dilaurate (0.88 g, 1%). The reaction mixture is stirred at room temperature, under nitrogen, for 2 hours. After this time the % NCO falls to zero as evidenced by the disappearance of the 2170 cm⁻¹ absorption in the infrared. The product is a clear, colorless oil with the following structure:

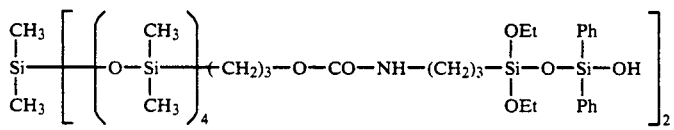

EXAMPLE 11

Preparation of Polysiloxane Coating for Glass

The poly(dimethylsiloxane) TEOS macromer of Example 10 (11.1 g, 8.4 mmol) is vigorously stirred under nitrogen at 100° C. with diphenylsilanediol (3.6 g, 16.8 mmol). After one hour a clear, colorless, liquid coating composition is obtained with the following structures:

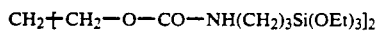

Stannous octoate (0.15 g, 1%) is dissolved in the coating composition which is subsequently coated at 3 mil (0.076 mm) thickness on a clear glass plate and cured at 130° C. for 1.5 hours. The rubbery coating obtained is resistant to delamination upon exposure to boiling water for 24 hours.

EXAMPLE 12

Preparation of Bis(Sulfide) TEOS Macromer 1,4-Dibromobutane (10.8 g, 50 mmol) is dissolved in 30 g of 2-pentanone along with 3-mercaptopropyltrimethoxysilane (19.6 g, 100 mmol). Potassium carbonate (13.8 g, 100 mmol) is added and the reaction mixture is vigorously stirred in a sealed glass reactor at 106° C., under nitrogen, overnight. After cooling the reaction product to room temperature and removing the potassium salts by filtration, the solvent is stripped under reduced pressure yielding the liquid macromer with the following structure:

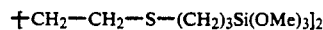

EXAMPLE 13

Preparation of Bis(Sulfide)-Siloxane Coating for Glass

The bis (sulfide) TEOS macromer of Example 12 (4.5 g, 10.0 mmol) is vigorously stirred with diphenylsilanediol (4.3 g, 20.0 mmol) and dibutyltin dilaurate (0.26 g, 3.0%) in a sealed glass vessel at 100° C. After 10 minutes a clear, yellow, liquid coating composition is obtained with the following structure:

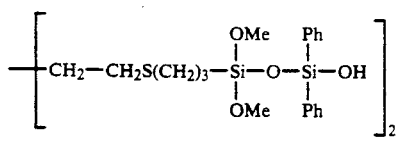

A 3 mil (0.076 mm) thickness film is drawn over a clean glass plate and cured in a 130° C. oven for 4 hours. A soft rubbery coating is obtained which is consistent to hydrolytic delamination upon exposure to boiling water for 48 hours.

EXAMPLE 14

Preparation of Bis(Amide) TEOS Macromer

Dimethyl adipate (8.7 g, 50 mmol) is charged into a 100 mL round bottomed flask equipped with distillation apparatus and nitrogen inlet. Then 3-aminopropyltriethoxysilane (22.1 g, 100 mmol) is added followed by two drops of a 25% solution of sodium methoxide in methanol. The vigorously stirred reaction mixture is heated to 180° C. overnight. After 18 hours at this temperature, 3.7 g of methanol distillate is collected. The bis (amide) product is obtained as a clear, viscous liquid with the following structure:

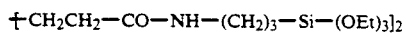

EXAMPLE 15

Preparation of Bis(Amide)-Siloxane Coating for Glass

The bis (amide) TEOS macromer of Example 14 (8.3 g, 15.0 mmol) is reacted at 100° C. with diphenylsilanediol (6.5 g, 30.0 mmol)and dibutyltin dilaurate catalyst (0.15 g, 1.0%) as described in Example 13. After 20 minutes a clear liquid coating composition is obtained with the following structure:

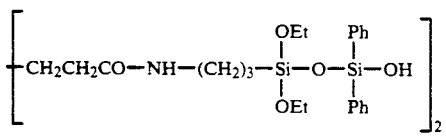

This composition is drawn over a clean glass plate at a thickness of 3 mils (0.076 mm) and cured at 130° C. for 3 hours. A hard coating is obtained which resists delamination exposure to boiling water for 14 hours.

Other TEOS adducts which may be used in place of the TEOS adduct of Example 2 are seen below.

| Example | TEOS-Adduct Structure |
|---|---|
| 16 | HN$+$(CH$_2$)$_3$Si(OEt)$_3$]$_2$ |
| 17 | [—CH$_2$CH$_2$NH((CH$_2$)$_3$Si(OEt)$_3$]$_2$ |
| 18 | [(—CH$_2$)$_3$—OCONH—(CH$_2$)$_3$Si(OEt)$_3$]$_2$ |
| 19 | [—CH$_2$Si(OEt)$_3$]$_2$ |
| 20 | S$+$(CH$_2$)$_3$Si(OEt)$_3$]$_2$ |
| 21 | [—CH$_2$CH$_2$S—(CH$_2$)$_3$Si(OEt)$_3$]$_2$ |
| 22 | (EtO)$_3$Si—O$+$Si(CH$_3$)$_2$—O$+_n$Si(OEt)$_3$ |
| 23 | 1,4-C$_6$H$_4$[C(=O)—NH(CH$_2$)$_3$Si(OEt)$_3$]$_2$ |
| 24 | (EtO)$_3$Si(CH$_2$)$_3$NH—C(=O)—(CH$_2$)$_3$Si(OEt)$_3$ |
| 25 | CH$_2$[CH$_2$—O—C(=O)—NH—(CH$_2$)$_3$Si(OEt)$_3$]$_2$ |
| 26 | (EtO)$_3$Si(CH$_2$)$_3$N$+$(CH$_2$)$_3$—O—C(=O)—CH$_2$)$_3$Si(OEt)$_3$]$_2$ |
| 27 | (EtO)$_3$Si(CH$_2$)$_3$S—(CH$_2$)$_3$—C(=O)—O(CH$_2$)$_3$Si(OEt)$_3$ |
| 28 | (EtO)$_3$Si(CH$_2$)$_3$NH(CH$_2$)$_3$—C(=O)—O—(CH$_2$)$_3$Si(OEt)$_3$ |
| 29 | O=C$+$NH(CH$_2$)$_3$Si(OEt)$_3$—]$_2$ |
| 30 | (EtO)$_3$Si(CH$_2$)$_3$NCH$_2$CH$_2$NHCONH(CH$_2$)$_3$Si(OEt)$_3$ <br> \| <br> C=O <br> \| <br> NH <br> \| <br> (CH$_2$)$_3$ <br> \| <br> Si(OEt)$_3$ |
| 31 | (EtO)$_3$Si(CH$_2$)$_3$CH[—C(=O)—NH—(CH$_2$)$_3$Si(OEt)$_3$]$_2$ |
| 32 | O=P—[NH(CH$_2$)$_3$Si(OEt)$_3$]$_3$ |
| 33 | (EtO)$_3$Si(CH$_2$)$_3$NH—S(=O)$_2$—C$_6$H$_4$—(CH$_2$)$_3$Si(OEt)$_3$ |
| 34 | (EtO)$_3$Si(CH$_2$)$_3$NHCONH(CH$_2$)$_6$NHCONH(CH$_2$)$_3$Si(OEt)$_3$ |
| 35 | (EtO)$_3$Si(CH$_2$)$_3$NHCONH(CH$_2$)$_4$NHCONH(CH$_2$)$_3$Si(OEt)$_3$ |

| | Example 36 | | | |
|---|---|---|---|---|
| TEOS-Adduct of Example | Adhesive Strength kg/cm$^2$ | Hardness (Shore-D) | Density (g/cm3) | Refractive Index |
| 24 | >45 (20% TiO2) <br> >45 (after 1 week at 100% humidity/93° C.) <br> 4 (after 2 days boiling water) <br> 12 (20% TiO2, after 5000 hours | 84 | (1.51) | 1.56 |

| Example 36 | | | | |
|---|---|---|---|---|
| TEOS-Adduct of Example | Adhesive Strength kg/cm² | Hardness (Shore-D) | Density (g/cm3) | Refractive Index |
| 25 | Weather-o-Meter) 16 (unpigmented, after 5000 hours Weather-o-Meter) >35 (20% carbon black) >24 (after 1 week at 100% humidity/93° C.) 3 (after 2 days boiling water) 11 (after 3000 hours Weather-o-Meter) 14 (unpigmented, after 3000 hours Weather-o-Meter) | | | |

Cured urea-siloxane coatings such as prepared in Example 7 exhibit the physical properties set forth below.

COMPARATIVE EXAMPLE A

Amino-terminated poly(propylene oxide), (Jeffamine D 230, Texaco Chemical Company), 23.8 g, is weighed into a 100 mL round bottomed flask along with 10.0 g of dry acetone. Then, 2-isocyanatoethyl methacrylate, 1 equivalent, (18.60 g) is added dropwise with vigorous stirring. After addition of benzoin methyl ether (16.0 mg), the acetone is evaporated under vacuum and the methacrylate terminated bis(urea) coating composition is drawn over the surface of a clean glass plate at a thickness of 3 mils (0.076 mm). The composition is subsequently cured by irradiating with three 15 watt BLACK RAY UV lights for two hours. A clear, hard, adherent (187 psi) coating is obtained. However, the coating is readily hydrolyzed off the glass after soaking in water at 90° C. for 1.0 hour.

What is claimed is:

1. A compound of formula I

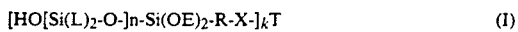

wherein
n is 1 to 100, and
L is methyl, isopropyl, —CH₂CH₂CF₃, tert-butyl, cyclohexyl or phenyl,
k is 2 to 4,
E is methyl or ethyl,
R is ethylene or trimethylene,
X is —NHCONH—, —NHCOO—, —S—, —NHCO— or a direct bond, where the —NH— groups is attached to R, and
T is, when k is 2 and X is a direct bond, —NHCONH—, or
T is, when X is —NHCONH—, the residue of a diisocyanate or a triisocyanate after removal of 2 or 3 NCO groups, or
T is, when X is —NHCOO—, the residue of a diol, triol or tetraol or of a poly(dimethylsiloxane)alkanepolyol after removal of 2, 3 or 4 OH groups or
T is, when X is —S—, alkylene of 1 to 12 carbon atoms, alkanetriyl of 3 to 8 carbon atoms or alkanetetrayl of 4 to 10 carbon atoms, or
T is, when X is —NHCO—, alkylene of 2 to 10 carbon atoms or arylene of 6 to 10 carbon atoms.

2. A compound according to claim 1 wherein
n is 1,
L is phenyl,
k is 2 or 3,
E is ethyl,
R is trimethylene,
X is —NHCONH—, —NHCOO—, —S— or —NHCO—,
when X is —NHCONH— T is a residue of a diisocyanate,
when X is —NHCOO—, T is a residue of a diol,
when X is —S—, T is alkylene of 1 to 8 carbon atoms, and
when X is —NHCO—, T is alkylene of 2 to 8 carbon atoms.

3. A compound according to claim 2 wherein X is —NHCONH—.

4. A compound according to claim 2 wherein, when X is —S—, T is alkylene of 2 to 4 carbon atoms.

5. A compound according to claim 2 wherein, when X is —NHCO—, T is alkylene of 4 to 6 carbon atoms.

6. A compound according to claim 1 wherein T is the radical derived from a diisocyanate, triisocyanate or mixture thereof selected from the group consisting of ethylene diisocyanate, 1,2-diisocyanato-propane, 1,3-diisocyanatopropane, 1,6-diisocyanatohexane, 1,2-diisocyanato-cyclohexane, 1,3-diisocyanatocyclohexane, 1,4-diisocyanatobenzene; bis (4-isocyanatocyclohexyl)methane, bis-(4-isocyanatocyclohexenyl) methane, bis(4-isocyanatophenyl)-methane, 1,2- and 1,4-toluene diisocyanate; 3,3'-dichloro-4,4'-diisocyanatobiphenyl; tris(4-isocyanatophenyl)methane, 1,5-diisocyanato-naphthalene, hydrogenated toluene diisocyanate; 1-isocyanatomethyl-5-isocyanato-1,3-3-trimethylcyclohexane (=isophorone diisocyanate); 1,3,5-tris(6-isocyanatohexyl) biuret, 1,6-diisocyanato-2,2-4-(2,4,4)-trimethyl-hexane, 2,2'-diisocyanatodiethyl fumarate; 1,5-diisocyanato-1-carboxypentane; 1,2-, 1,3-, 1,6-, 1,7-, 1,8-, 2,7- and 2,3-diisocyanatonaphthalene; 2,4- and 2,7-diisocyanato-1-methylnaphthalene; 1,4-diisocyanatomethylcyclo-hexane; 1,3-diisocyanato-6(7)-methyl-naphthalene; 4,4'-diisocyanatobiphenyl; 4,4'-diisocyanato-3,3'-dimethoxy-bisphenyl; 3,3'- and 4,4'-diisocyanato-2,2'-dimethyl biphenyl; bis-(4-isocyanatophenyl) ethane; and bis(4-isocyanatophenyl ether.

7. A compound according to claim 6 wherein T is the radical derived from a dicyclohexylmethane-4,4'-diisocyanate.

8. A compound of formula I according to claim 1 wherein n is 1, L is phenyl, k is 2 or 3, E is ethyl, R is trimethylene, X is —NHCONH— and T is a residue of a diisocyanate or a triisocyanate.

9. A compound according to claim 1 wherein T is the residue of a diol, triol or tetraol or of a poly(dimethylsiloxane) alkanepolyol selected from the group consisting of

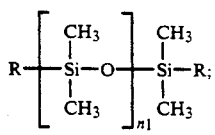

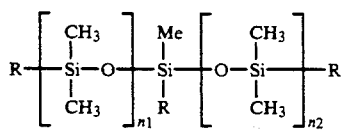

wherein

R is —CH$_2$CH$_2$CH$_2$OH, —CH$_2$CH$_2$CH(OH)CH$_3$, —(CH$_2$)$_3$—O—CH$_2$CH(OH)CH$_2$OH, —(CH$_2$)$_3$N(CH$_2$CH$_2$OH)$_2$), or —(CH$_2$)$_4$—CH(OH)CH$_2$OH, and $n_1$ and $n_2$ are integer from 2 to 50, with the proviso that $n_1$ and $n_2$ is not greater than 60%, or of 1,2 Butanediol, 1,3-butanediol, 1,4 butanediol, 1,2-cyclohexane diol, 1,2-cyclooctanediol, 1,3-cyclopentanediol, 1,2-decanediol, 1,10-decanediol, dicyclohexyl-4,4'-diol, 2,2-diethyl-1,3-propane diol, 2,5-dimethyl-2,5-hexanediol, 2,4-dimethyl-2,4-pentane diol, ethylene glycol, 1,7-heptanediol, 1,2-hexanediol, 1,5-hexanediol, 1,6-hexanediol, 2-methyl-2,4-pentanediol, 1,8-octanediol, pentaerythritol, 1,5-pentanediol, 1,14-tetradecanediol, polyethylene glycol, polypropylene glycol, polybutylene glycol, neopentyl glycol, trimethyololpropane.

10. The compound of formula I according to claim 1 which is

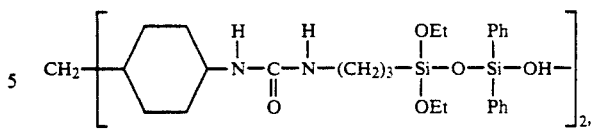

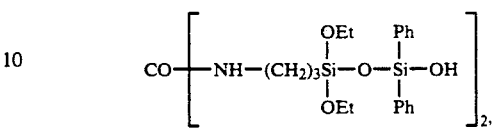

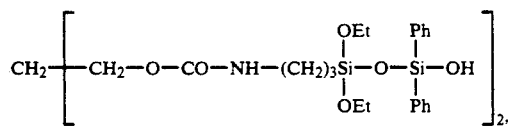

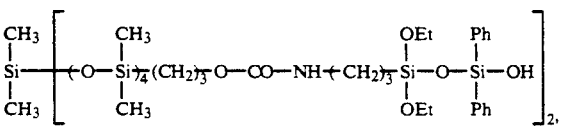

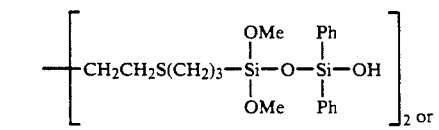

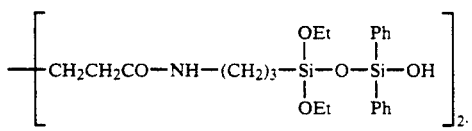

* * * * *